United States Patent [19]

Thomason et al.

[11] Patent Number: 4,606,225
[45] Date of Patent: * Aug. 19, 1986

[54] METHOD FOR NONDESTRUCTIVE TESTING OF COATING ADHESION

[75] Inventors: William H. Thomason; Randall G. Ivie, both of Ponca City, Okla.

[73] Assignee: Conoco Inc., Ponca City, Okla.

[*] Notice: The portion of the term of this patent subsequent to May 6, 2003 has been disclaimed.

[21] Appl. No.: 669,127

[22] Filed: Nov. 7, 1984

[51] Int. Cl.$^4$ .............................................. G01N 19/04
[52] U.S. Cl. ...................................... 73/150 A; 73/827
[58] Field of Search ...................... 73/150 A, 827, 837; 156/155

[56] References Cited

U.S. PATENT DOCUMENTS

| | | | |
|---|---|---|---|
| 2,711,775 | 6/1955 | Batchelor et al. | 156/344 |
| 3,527,093 | 9/1970 | Sellers | 73/150 A |
| 3,577,775 | 5/1971 | Henderson | 73/827 |
| 3,628,378 | 12/1971 | Regan, Jr. | 73/827 |
| 3,821,892 | 7/1974 | Saberg | 73/150 A |
| 4,381,248 | 4/1983 | Lazar | 156/155 |
| 4,413,510 | 11/1983 | McCusker et al. | 73/150 A |
| 4,487,643 | 12/1984 | Ellett | 156/155 |

Primary Examiner—Charles Frankfort
Assistant Examiner—W. Morris Worth
Attorney, Agent, or Firm—Stephen A. Littlefield

[57] ABSTRACT

A method of coating testing comprises applying a consistantly perpendicular minimum tension force to a dolly for testing to see if the adhesive bond strength between a coating and a substrate meets a minimum specification for such bond. The tester comprises a ram passing through an axially centered opening in a dolly bonded to the coating. A piston and cylinder are associated with the ram and the dolly so that pressure within the piston chamber formed thereby causes the development of a tension force within the dolly which is perpendicular to the coating being tested because of the coaxially centered orientation of the dolly with respect to the ram. The pressure is increased only to a point wherein the tension force is equal to a minimum specification for bonding adhesion. If the coating has not separated from the substrate, the bond therebetween meets the specification. The testing apparatus may then be removed by causing the bonding agent attaching the dolly to the coating to fail as by heating.

7 Claims, 3 Drawing Figures

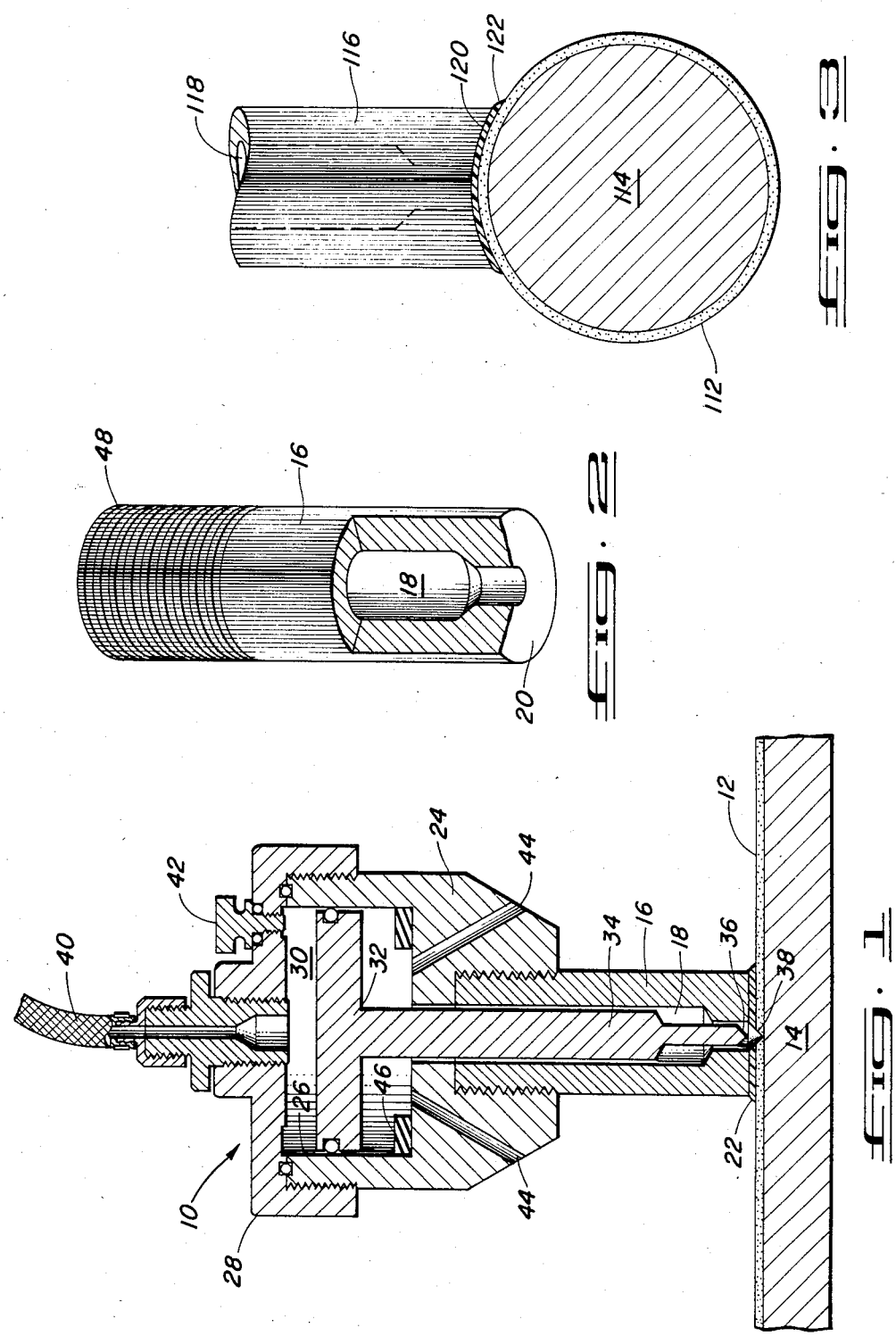

METHOD FOR NONDESTRUCTIVE TESTING OF COATING ADHESION

This invention relates to the art of materials testing and, more particularly, to a process for the nondestructive testing of coating adhesion to a substrate.

BACKGROUND OF THE INVENTION

For many applications, the adhesion of an exterior coating to a substrate is extremely critical. Whether the coating is for electrochemical protection such as an anodic coating of flame sprayed aluminum on a steel offshore structure or to provide barrier protection or decorative enhancement such as a paint coating on a structure to be protected, it is critical that the adhesion of the coating to the substrate be within well defined limits, depending on the application, in order to provide the requisite protection desired of the coating. Any protective advantage afforded by a coating is quickly lost when the coating separates from the substrate.

In order that the tests be reliably reproducible, it is essential that an adhesion tester apply purely tensile forces to the coating which are in a direction perpendicular to the coated surface. Any nonperpendicularly-directed forces can result in tearing of the coating and an inaccurate adhesion test reading.

U.S. Pat. No. 3,821,892 describes an apparatus for testing intercoat adhesion. A dolly is bonded to the test material and a tractive force is applied to the dolly which is located between a two-legged support, the legs bearing against the coated surface. While this apparatus is adequate for testing coatings on a completely flat surface, any localized irregularities within the span of the legs or any curvature in the part being tested can cause a coating to tear. U.S. Pat. Nos. 3,628,378 and 3,577,775 disclose apparatus of similar operation.

While the above-noted apparatus do provide an investigator with useful information regarding coating adhesion, the testing process, of necessity, results in the removal of at least a portion of the tested coating. Such coating removal thus at least partially destroys the usefullness of the article to which the coating is applied because of the destructive nature of the test. For this reason, coating adhesion tests on articles to be later placed in use must be made only in a very limited number of areas and only in those areas in which the holiday in the coating which is created does not present a critical problem.

SUMMARY OF THE INVENTION

The present invention provides a method of tensile adhesion testing of a coating to a substrate in which a force perpendicular to the tested material can be applied in a multiplicity of desired points on the tested structure in order to determine if the coating adhesion meets minimum specification requirements.

In accordance with the present invention, a method of testing an adhesive bond of a coating to a substrate in a tensile mode in order to determine if the adhesive bond meets minimum specifications comprises the steps of providing a dolly having an axially centered opening therethrough and bonding the dolly to the coating with bonding means having a bond strength in excess of the strength of the adhesive bond between the coating and the substrate. Piston and cylinder means are then attached to the dolly, the piston and cylinder means include an axially centered ram, the ram passing through the axial opening of the dolly. Pressure is then applied to the piston and cylinder means to force the ram into pressure engagement with the coating. The pressure is increased and monitored to a pre-determined point such that the tensional force applied to the dolly correlates with the minimum specification for the adhesive bond and ceasing the increasing pressure when the minimum specification is achieved.

Still further in accordance with the invention, the above-noted method includes the final step of causing the bonding means to fail so that the dolly can be removed without destruction of the coating.

It is therefore an object of this invention to provide a method whereby the adhesion of a coating to a substrate can be tested in a multiplicity of areas over an entire structure without destroying the desired protective properties of the coating.

It is yet another object of this invention to provide a method whereby the adhesion of a coating to a substrate may be tested without the destruction of the adhesive bond between a coating and a substrate which meets a minimum specification for adhesion.

BRIEF DESCRIPTION OF THE DRAWINGS

These and other objects of the invention will become apparent through a more detailed description of the invention and with reference to the accompanying drawings forming a part of this specification and in which:

FIG. 1 is a schematic, cross-sectional view of an adhesion tester used in accordance with the method of the present invention;

FIG. 2 is a perspective view of a dolly used in a preferred form of the apparatus employed in the method of the present invention, and FIG. 3 shows an alternative form of dolly in the testing mode of the present invention.

DETAILED DESCRIPTION OF THE PREFERRED EMBODIMENTS AND DRAWINGS

Referring now to the drawings wherein the showings are presented for the purposes of illustrating a preferred embodiment of the invention only and not for the purpose of limiting same, FIG. 1 shows an adhesion tester 10 in position for testing the adhesive bond between a coating 12 and a substrate 14. It will be understood that the coating 12 may be any type of coating such as a paint, a plastic laminate, or a metal coating applied by any of several processes such as flame spraying, electroplating, and the like. Similarly, the substrate 14 may be wood, a polymeric material, or metal. For purposes of illustrating a preferred embodiment, the coating 12 comprises a flame sprayed aluminum coating on a substance 14 of steel.

In accordance with the invention, a dolly 16 having an axially centered bore 18 and a bonding face 20 (FIG. 2) is provided. The dolly 16 is bonded on its bonding face 20 to the coating 12 with bonding means such as a layer of epoxy 22 extending between the surface of the coating 12 and the bonding face 20 of the dolly 16. Although the bonding means 22 is preferred to be an epoxy, any type of adhesive material may be used, the criteria for selection of a bonding material being that the adhesive strength of the bonding means 22 between both the coating 12 and the bonding face 20 of the dolly 16 exceeds the adhesive bond strength of the coating 12 to the substrate 14. As shown in the figures, the dolly is preferably cylindrical in form but, it will be understood that practice may dictate other forms which may be used so long as the bore 18 is axially centered in the dolly.

After the dolly 16 has been securely bonded to the coating 12, the dolly is attached to the tester assembly 24. A portion of the tester assembly 24 includes a cylindrical inner surface 26 and a cap 28 defining a piston chamber 30. A piston 32 is disposed within the piston chamber 30 and has an axially centered ram 34 attached thereto and extending outwardly of the tester assembly 24 through the axially centered opening 18 of the dolly 16. The ram 34 is shown having a pointed end portion 36 which will engage the coating 12. The pointed form of the ram 34 is preferred if the formation of a dimple 38 in the coating 12 is not critical since the point 36 acts to positively locate the axially centered ram 34 so that a consistantly perpendicular tensional force is developed in the dolly 16. The minor dimple 38 left in the coating 12 would not present a critical destruction of the coating for applications such as flame sprayed aluminum coatings applied to steel structures for offshore cathodic protection since the minor holiday in the coating would be electrochemically protected by the remainder of the coating. However, in applications where dimpling of the coating is to be avoided such as in a decorative coating, the pointed end 36 of the ram 34 would need to be adapted to a blunt form which would not penetrate or dimple the coating 12.

Pressurized fluid is admitted to the piston chamber 30 through a conduit 40 which is attached to some type of fluid pressurizing means (not shown) such as a hydraulic pump, an air pump or the like. Various other features may be provided in the tester assembly such as a bleed off valve 42 for relieving pressure within the piston chamber 30 as well as various vent passages 44 for relieving pressure within the cylinder 26 on the side of the piston 32 opposite the piston chamber 30. Bump stops 46 may also be provided to limit the travel of the piston 32 and the ram 34.

In operation of the testing apparatus to test the tensile bond strength of the coating 12 through the substrate 14, pressurized fluid is admitted to the piston chamber 30 and the pressure is monitored by any common means. The pressure within the piston chamber 30 drives the piston 32 and its attached ram 34 into engagement with the surface of the coating 12. An increase in fluid pressure thus causes a tensional force to be developed in the dolly and, thereby, in the bonding means 22 and in the coating 12 as well. Because of the axially centered configuration of the ram 34 within the dolly 16, such tensional forces are applied perpendicular to the surface of the coating 12.

The testing of the coating adhesion continues by increasing the pressure within the piston chamber 30 while monitoring the increase in pressure. The ratio of the area of the piston 32 to the area of the bonding face 20 of the dolly 16 is known so that the minimum pressure within the piston chamber 30 required to meet the tensional coating adhesion specification of the coating 12 to the substrate 14 can be calculated. The fluid pressure in the chamber 30 is thus increased to that point and, assuming that the coating adhesion has not failed up to the point, it can be said that the coating meets the desired adhesion specification.

FIG. 3 illustrates an alternative form of dolly 116 which has a bonding face 120 which is curved to conform to the shape of the surface of a circular member rather than a planer member as shown in the previous figures. The dolly 116 is bonded to the surface of a coating 112 on a substrate 114 utilizing bonding means 122 which may be any type as previously described with respect to the earlier figures. The dolly 116 has an axially centered bore 118 shown in phantom 4 accepting the ram 34 of the tester assembly 24 as previously described. It can be clearly seen that the axially centered nature of the ram 34 within the central bore 118 of the dolly 116 will cause the development of a perpendicular tensional force to test the adhesion of the coating 112 to the substrate 114.

Following the successful testing of the coating, the tester assembly 24 is removed from the dolly. In tested structures in which the presence of a dolly bonded to the surface of the coated structure would present no difficulty, the dolly 16 can be left bonded to the coating 12 and the structure can be placed in use. However, with most applications, it is desirable to remove the dolly 16 following a test.

In accordance with a preferred embodiment of the invention, a dolly 16 is removed from the coating 12 by causing the bonding means 22 to fail thereby leaving the coating 12 on the substrate 14 in tact. One preferred method for causing the bonding means 22 to fail is to heat it above a critical temperature at which point the dolly 16 may be removed. The heating may be carried out by any of several means such as direct application of heat to the bonding means 22 by a torch or, preferably, heating the remote, threaded end 48 (FIG. 2) so that heat is gradually conducted through the dolly 16 to the bonding face 20 and the bonding means 22 heated thereby to its critical temperature. This process minimizes the heating of the coating 12 on the substrate 14 which may in some way alter its protective properties.

The bonding means 22 may also be caused to fail by any other mechanism which is appropriate to the bonding means selected. Thus, a bonding means which is attacked by a solvent may be caused to release the dolly 16 by the application of such solvent to the bonding means 22. Fracture of a brittle bonding means 22 may also be possible which the application of a properly directed impact force if such impact will avoid damage to the coating 12.

EXAMPLE

The apparatus shown in FIGS. 1 and 2 was utilized to test the coating adhesion of a flame sprayed aluminum coating applied to a steel substrate. The minimum specification for adhesive bond strength between the aluminum coating and the steel substrate for offshore oil production risers is 1,000 psi. The dolly face had a surface area of 0.75 inch. The dolly was bonded to the surface of the flame sprayed aluminum coating using a cyanoacrylate adhesive designated CA-5 sold by 3M Company. The bond was allowed to cure for 24 hours although 80% of the bond strength may be reached after 1 to 2 hours. The CA-5 adhesive is rated at a tensile strength of up to 5,000 psi. The coating testing apparatus was then attached to the dolly and the pressure in the piston chamber was increased until a gauge pressure of 270 psi was noted. Based on the size of the piston and surface area of the dolly, the calculated tensile loading was 1,010 psi. Since the coating did not separate from the substrate at this pressure, the coating successfully met the specification.

While the invention has been described in more limited aspects of the preferred embodiment thereof, other embodiments have been suggested and still others will occur to those skilled in the art upon the reading and understanding of the foregoing specification. It is intended that all such embodiments be included within the scope of this invention as limited only by the appended claims.

Having thus described my invention, I claim:

1. A method of testing an adhesive bond of a coating to a substrate to meet a minimum specification in a tensile mode comprising the steps of providing a dolly having an axially centered opening therethrough; bonding the dolly to the coating with bonding means having a bond strength in excess of an adhesive bond strength of an adhesive bond between the coating and the substrate; attaching piston and cylinder means to the dolly, the piston and cylinder means including an axially centered ram, the ram passing through the axially centered opening of the dolly; applying pressure to the piston and cylinder means to force the ram into pressure engagement against the coating and increasing the pressure to a predetermined monitored pressure at which a tensile force developed in the dolly meets the minimum specification.

2. The method as set forth in claim 1 further including the step of removing the piston and cylinder means and the ram from the dolly.

3. The method as set forth in claim 2 further including the step of causing said bonding means to fail following completion of the testing.

4. The method as set forth in claim 3 wherein said step of causing said bonding means to fail comprises heating said bonding means.

5. The method as set forth in claim 4 wherein the step of heating said bonding means comprises heating said dolly at a point remote from said bonding means.

6. The method as set forth in claim 3 wherein said step of causing said bonding means to fail comprises striking said dolly such that an impact from the striking causes the bonding means to shatter.

7. The method as set forth in claim 3 wherein said step of causing said bonding means to fail comprises solvating said bonding means with a solvent.

* * * * *